United States Patent
Gokaraju et al.

(10) Patent No.: US 9,301,987 B2
(45) Date of Patent: Apr. 5, 2016

(54) **ANTI-ADIPOGENIC COMPOSITIONS CONTAINING *PIPER BETLE* AND *DOLICHOS BIFLORUS***

(75) Inventors: Ganga Raju Gokaraju, Vijayawada (IN); Rama Raju Gokaraju, Vijayawada (IN); Trimurtulu Golakoti, Vijayawada (IN); Krishanu Sengupta, Vijayawada (IN); Kiran Bhupathiraju, Vijayawada (IN); Venkata Krishna Raju Alluri, Vijayawada (IN)

(73) Assignee: LAILA NUTRACEUTICALS, Vijayawada (IN)

( * ) Notice: Subject to any disclaimer, the term of this patent is extended or adjusted under 35 U.S.C. 154(b) by 500 days.

(21) Appl. No.: 12/679,826

(22) PCT Filed: Sep. 24, 2007

(86) PCT No.: PCT/IN2007/000429
§ 371 (c)(1),
(2), (4) Date: Mar. 24, 2010

(87) PCT Pub. No.: WO2009/040824
PCT Pub. Date: Apr. 2, 2009

(65) Prior Publication Data
US 2010/0203117 A1    Aug. 12, 2010

(51) Int. Cl.
| | | |
|---|---|---|
| *A61K 36/67* | (2006.01) | |
| *A23L 1/29* | (2006.01) | |
| *A23L 1/30* | (2006.01) | |
| *A61K 36/185* | (2006.01) | |
| *A61K 36/328* | (2006.01) | |
| *A61K 36/48* | (2006.01) | |
| *A61K 36/9068* | (2006.01) | |

(52) U.S. Cl.
CPC .............. *A61K 36/67* (2013.01); *A23L 1/293* (2013.01); *A23L 1/3002* (2013.01); *A61K 36/185* (2013.01); *A61K 36/328* (2013.01); *A61K 36/48* (2013.01); *A61K 36/9068* (2013.01)

(58) Field of Classification Search
None
See application file for complete search history.

(56) References Cited

U.S. PATENT DOCUMENTS

| | | | |
|---|---|---|---|
| 5,698,199 A | 12/1997 | Mori | |
| 5,916,567 A * | 6/1999 | Neelakantan | 424/757 |
| 6,413,553 B1 | 7/2002 | Bandyopadhyay | |
| 6,531,115 B1 | 3/2003 | Singh | |
| 6,531,166 B2 | 3/2003 | Bandyopadhyay | |
| 6,610,332 B2 | 8/2003 | Bandyopadhyay | |
| 6,967,034 B2 | 11/2005 | Bandyopadhyay | |
| 7,045,157 B2 | 5/2006 | Bandyopadhyay | |
| 2005/0089585 A1* | 4/2005 | Bandyopadhyay | A61K 31/215 424/727 |
| 2006/0134231 A1 | 6/2006 | Hines et al. | |

FOREIGN PATENT DOCUMENTS

| | | |
|---|---|---|
| JP | 11130685 A | 5/1999 |
| JP | 2000290165 A | 10/2000 |
| JP | 2000302797 A * | 10/2000 |
| JP | 2005082546 A * | 3/2005 |
| JP | 2005325025 A * | 11/2005 |
| WO | WO2006068777 A3 | 6/2006 |

OTHER PUBLICATIONS

Bherata Bhaitajya Ratnekara. Compiled by Nagonadesa Chaganalela'eha ,Translated by Gopinath Gupta—vol. I • B. Jain Publishers, New Delhi, Edn. 2nd. Reprint, Aug. 1999, p. 337 (please note that the citation appears at the bottom of the page of the translation).*

Amin et al. "The Protective Effect of Tribulus terrestris in Diabetes". Annals of the New York Academy of Sciences, vol. 1084, Issue 1 (Nov. 28, 2006) 391-401.*

"H"drogepathya". From: ¡ryabhi¾aka—Gujarati Edited (Hindustc /na No Vaidyareja) Translation by Harikrishna Bhagwan Lal Vyas; Sastu Sahitya Vardhaka Karyalaya, Bhadra, Ahmedabad, Edn. 12th, 1957" p. 154.*

"WorldHealth.net: Tribulus Terrestris". Posting date: Dec. 30, 2005 [Retrieved from the Internet on: Apr. 20, 2012]. Retrieved from the Internet: <URL: http://www.worldhealth.net/news/tribulus_terrestris_puncture_vine_fruit/>.*

Oudhia, P. "Punarrnava or Santhi (Boerhaavia diffusa Linn.)". Internet archive date: Jul. 6, 2004 [Retrieved from the Internet on: Apr. 20, 2012]. Retrieved from the Internet: <http://web.archive.org/web/20040706030702/http://www.hort.purdue.edu/newcrop/CropFactSheets/punanrnava.html>.*

(U1) Sharma, D. Web Date: Jun. 15, 2007. [Retrieved from the Internet on: Apr. 20, 2012]. Retrieved from the Internet: <URL: http://abchomeopathy.com/forum2.php/113481/>.*

(Continued)

*Primary Examiner* — Amy L Clark
(74) *Attorney, Agent, or Firm* — Kramer & Amado, P.C.

(57) ABSTRACT

Herbal compositions are useful for inhibition, amelioration or prevention of adipogenesis mediated diseases such as obesity, lipid storage disease and hyperlipemia. The herbal compositions comprise biologically effective amounts of extracts or fractions from *Piper betle* in combination with one or more of the extracts or fractions derived from *Dolichos biflorus, Commiphora mukul, Boerhaavia diffusa, Tribulus terrestris* and *Zingiber officinale* as active ingredients. The compositions optionally contain a bio-enhancing agent or a bio-protecting agent, along with biologically acceptable carriers or diluents. The herbal compositions may be used in a method for treating or preventing adipogenesis involved diseases in mammals.

28 Claims, 4 Drawing Sheets

(56) References Cited

OTHER PUBLICATIONS (V1) Mohanty et al. "Effect of Curcuma longa and Ocimum sanctum on myocardial apoptosis in experimentally induced myocardial ischemic-reperfusion injury". BMC Complementary and Alternative Medicine, vol. 6, No. 3 (2006) pp. 1-12.*
(W1) Arambewela, LSR et al. "Antidiabetic activities of aqueous and ethanolic extracts of Piper betle leaves in rats". Journal of Ethnopharmacology. vol. 102, Issue 2 (2005) 239-245.*
(X1) "Dawa E—Kulthi Barae Ziyabitus" from Khazaain-al-Advia, vol. III (20th century AD), Nadeem Yunus Printer / Sheikh Mohd Basheer & Sons, Lahore, 1926 AD. p. 375.*
Indian J Pharmacoll Apr. 2006; vol. 38, Issue 2, 131-2.*
Arambewela et al. International Journal of Food Science and Technology 2006, 41 (Supplement 1), 10-14.*
Singh et al. Cardiovascular Drugs and Therapy 1994;8:659-664.*
(U1) Satheesh et al. Journal of Herbs, Spices & Medicinal Plants. vol. 10, Issue 4, 2004.*
(V1) Pandey et al. Pharmaceutical Biology. 2007, vol. 45, No. 8, pp. 619-625.*
(W1) Stoilova et al. Food Chemistry 102 (2007) 764-770.*
(X1) Lak¾am¤vilésarasa. From: Bhai¾ajya Ratnévalа—Edited by Rajeshvaradutta Shastri, Translated by Ambikaduttashastri : Chaukhamba Sanskrit Sansthan, Varanasi, Edn. 14th, 2001. [This book contains backr eferences from 1000 B.C.to 18th century]. Retrieved from TKDL on Apr. 28, 2015.*
(U2) Medoroge Pathya. From: Basavarèj¤yam—Chaukhambha Sanskrit Pratisthan, Delhi;Edn. $1^{st}$ Reprint ;2005 [Time of origin 15th century ] prior art p. 275. Retrieved from TKDL on Apr. 28, 2015.*
(V2) Punarnavédikvétha$^{mt;epmubaubxmx}$. From: Vndamc /dhava;—Marathi translated by Datto vallala Borkar;Yagyeswara Gopal Dixit, Bookseller, Pune;Edn. 1922 [Time of origin 9th century ] prior art p. 415. Retrieved from TKDL on Apr. 28, 2015.*
(W2) Vanga Shodhana. From: Rasendracintéma'ai$^{mt;epmubaubxmx}$ Trans. Siddhinandan Mishra,—Chaukhamba Orientalia(Varanasi) Ed. 1st 1999 prior art p. 69-70. Retrieved from: TKDL on Apr. 28, 2015.*
(X2) Saravanan et al. Pharm Biol. 2004, vol. 42, Nos. 4-5, pp. 323-327.*
Kali Dasa; Vaidyamandrama,—with Hindi translation : Central Council for Research in Ayurveda & Sidhha Govt. of India Edn 2005, p. 63.
Yogarantnakarah—Commentary by Laksmipatisastri, Edited by Brahmasankara Sastri, ChaukhambaSanskrit Sansthan (Varanasi) Ed. 7th 2002 p. 43.
Sodhala; Sodhalanighantuah—(Namasamgraha Va Gunasamagraha) Edited by P.V. Sharma, Oriental Institute, Baroda, Edn 1st 1978 p. 174.
Bharata Bhaisajya Ratnakara—Compiled by Naginadasa Chaganalala Saha, Translated by Gopinath Gupta—vol. II:B Jain Publishers, New Delhi, Edn. 2nd Reprint, Aug. 1999. p. 42.
Govt of India: The Ayrvedic Phamacopoeia of India—Part I, Edn. 1st Reprinted 2001, Govt of India, Ministry of Health & Family Welfare, Dept of I.S.M. & H., New Delhi, p. 43.
Bharata Bhaisajya Ratnakara—Compiled by Naginadasa Chaganalala Saha, Translated by Gopinath Gupta vol. III B. Jain Publishers, new Delhi, Edn 2nd Repritng, Aug. 1999, p. 134.
Rasatantrasarah Evam Siddhaprayogasamgrahah; Part I; Krishan Gopal Ayurveda Bhawan Edn. 8th 1990 p. 472.
WHO's fact sheet No. 311, Sep. 2006, http://www.who.int/ mediacentre/factsheets/fs311/en/index.html.
H. G. Preuss, et al, Efficacy of a novel, natural extract of (−)-hydroxycitric acid (HCA-SX) and a combination of HCA-SX, niacinbound chromium and Gymnema sylvestre extract in weight management in human volunteers: A pilot study. Nutrition Research, 2004, 24, 45-48.
C. A. Haller and N. L. Benowitz. Adverse cardiovascular and central nervous system events associated with dietary supplements containing ephedra alkaloids, New England J. Medicine, 2000, 343, 1833-1838.
Ziuozenkova et al., Lipolysis of triglyceride-rich lipoproteins generates PPAR ligands: Evidence for an antiinflammatory role for lipoprotein lipase. PNAS, Mar. 4, 2003, Vol, 100, No. 5, 2730-2735.
Thomas. GN, The Trp64Arg polymorphism of the b3-adrenergic receptor gene and obesity in Chinese subjects with components of the metabolic syndrome. International Journal of Obesity, (2000) 24, 545-551.
Peter Arner, The β3-Adrenergic Receptor—A Cause and Cure of Obesity? The New England Journal of Medicine, (1995) 333, 382-383.
Glossary of Indian Medicinal Plants, pp. 195, 1996.
Saravanan R, et. al., Effect of Piper betle Leaf Extract on Alcoholic Toxicity in the Rat Brain, Journal of Medicinal Food 2003, vol. 6, 261-265.
Rathee JS, et. al.; Antioxidant Activity of Piper betel Leaf Extract and Its Constituents, J Agric Food Chem. 2006; 54 (24):9046-54.
Bhattacharya, S., et. al., Radioprotective Property of the Ethanolic Extract of Piper Betel Leaf, J. Radiation Research, 2005. 46(2), 165-171.
Arembewela et ai., Antidiabetic activities of aqueous and ethanolic extracts of Piper betie leaves in rats, J. Ethanopharmacology, 2005, 102, 239-245.
Santhakumari et. al., Antihyperglycemic Activity of Piper betle Leaf on Streptozotocin-Induced Diabetic Rats, J. Medicinal food, 2006, 9, 108-112.
Saravanan et al., Effect of Piper betel on Blood Glucose and Lipid Profiles in Rats After Chronic Ethanol Administration, Pharmaceutical Biology, 2004, 42, 323-327.
Muthu, AK, et. al., Antioxidant potential of methanolic extract of Dolichos biflorus Linn in high fat diet fed rabbits, Indian J. Pharmacol., 2006, 38(2): 131-132.
Muthu AK, et al., Hypolipidemic effect of methanolic extract of Dolichos biflorus Linn. in high fat diet fed rats, Indian J. Expt. Bioi. 2005. 43, 522-525.
Ogden et al., Prevalence of Overweight, Obesity and Extreme Obesity Among Adults: United States, Trends 1960-1962 Through 2007-2008 (http://www.cdc.gov/nchs/data/hestat/obesity_adult_07_08/ obesity_adult_07_08.htm.) Viewed Jan. 9, 2012.
Obesity and Overweight. WHO's fact sheet No. 311, Sep. 2006 (Updated Mar. 2011), (http://www.who.int/mediacentre/factsheets/ fs311/en/index.html) Viewed Jan. 9, 2012.
Tackling overweight and obesity in men in Europe (http://www. emhf.org/resource_images/obesity.pdf) Viewed Jan. 9, 2012.
Obesity (http://www.euro.who.int/en/what-we-do/health-topics/ noncommunicable-diseases/obesity#) Viewed Jan. 9, 2012.
Deborah Reynolds, TC1600 New Matter Training. Technology Center 1600 Symposium, Oct. 2005.
Sucrose Octanoate Esters, Techinical Evaluation Report, Mar. 9, 2005, Compiled by ICF Consulting, Inc., for the USDA National Organic Program.
Hossain, et al., "Purfication, Characterization and N-terminal Sequence Analysis of Betel Leaf (Piper betle) Invertase", Journal of the Chinese Chemical Society, 2011, 58, pp. 389-397.
Khmelnitsky, et al., "Relationship betweekn surface hydrophilicity of a protein and its stability against denaturation by organic solvents", FEBS Letters, vol. 284, No. 2, 267-269, 1991.
Uversky, et al., "Conformational transitions provoked by organic solvents in B-lactoglobulin: can a molten globule like intermediate be induced by the decrease in dielectric constant?", Folding & Design, Apr. 24, 1997, vol. 2, No. 3, pp. 163-172.
Burnett, "An Account fot eh Effect of Mercurial Vapours on the Crew of His Majesty's Ship Triumph, in the Year 1810", Philosophical Transactions of the Royal Society of London, vol. 113 (1823), pp. 402-408.
Waldron, "Did the Mad Hatter have mercury poisoning?", British Medical Journal, vol. 287, Dec. 24-31, 1983.
Young, et al., "Neurotoxic Mechanism of Cinnabar and Mercuric Sulfide on the Vestibulo-Ocular Reflex System of Guinea Pigs", Toxicological Sciences, 67, 256-263 (2002).

* cited by examiner

A: Protective efficacy

B: Therapeutic efficacy

ANTI-ADIPOGENIC COMPOSITIONS CONTAINING *PIPER BETLE* AND *DOLICHOS BIFLORUS*

TECHNICAL FIELD OF INVENTION

The present invention relates to herbal compositions for inhibition, amelioration or prevention of adipogenesis mediated diseases such as obesity, lipid storage disease and hyperlipemia, comprising, biologically effective amounts of extracts or fractions from *Piper betle* in combination with one or more of the extracts or fractions derived from *Dolichos biflorus, Commiphora mukul, Boerhaavia diffusa, Tribulus terrestris* and *Zingiber officinale*, as active ingredients and optionally containing a bio-enhancing agent or a bioprotecting agent along with biologically acceptable carriers or diluents. The invention further relates to a method for treating or preventing adipogenesis involved diseases in mammals using the invented compositions.

BACKGROUND OF THE INVENTION

Obesity is excess body weight for a particular age, sex and height as a consequence of imbalance between energy intake and energy expenditure. The primary cause of obesity is either due to overeating, inadequate exercise or eating disorder, some genetic disorders, underlying illness (e.g., hypothyroidism), certain medications, sedentary lifestyle, a high glycemic diet (i.e., a diet that consists of meals that give high post-prandial blood sugar) weight cycling (caused by repeated attempts to lose weight by dieting, eating disorders), stress and insufficient sleep.

During the past 20 years, obesity among adults has risen significantly in the United States. The latest data from the National Center for Health Statistics show that 30 percent of U.S. adults of 20 years of age and older, i.e. over 60 million people, are obese. The percentage of young people who are overweight has more than tripled since 1980. More than 16% of the children and teens aged 6-19 years, that is over 9 million young people, are considered overweight. Although, the US national health objectives for the year 2010 is to reduce the prevalence of obesity among adults to less than 15%, current data indicate that the situation is worsening rather than improving (http://www.cdc.gov/nchs/products/pubs/pubd/hestats/overweight/overwght_adult_03.htm). Obesity in Europe was recognized as a serious problem, with up to 27% of men, 38% of women and 3 million children are clinically obese (http://ec.europa.eu/health/ph_determinants/life_style/nutrition/green-papmutritiongp_c0183_en.pdt). The obesity was not limited to developed countries, but it was rapidly becoming a problem in developing countries as well.

As per World Health Organization's (WHO) latest projections, approximately 1.6 billion adults (age 15+) were overweight and at least 400 million adults were obese globally in 2005. WHO further projects that by 2015, approximately 2.3 billion adults will be overweight and more than 700 million will be obese (WHO's fact sheet No. 311, September 2006, http://www.who.int/mediacentre/factsheets/fs311/en/index.html).

Recent studies have shown that approximately a third of variance in adult body weights results from genetic influences. Leptin, an adipocyte and placenta-derived circulating protein, regulates the magnitude of fat stores in the body leading to obesity. Gastrointestinal peptides, neurotransmitters and adipose tissue may also have an etiologic role in obesity. Obesity and adipose tissue expansion increase the risk of hypertension, type 2 diabetes, arthritis, elevated cholesterol, cancer and serious hormonal imbalances in women, leading to sterility. Obesity also increases the risk of, dyslipidemia (for example, high total cholesterol or high levels of triglycerides), gallbladder disease, osteoarthritis, sleep disorders, respiratory problems, arteriosclerosis and heart failure.

Obesity is the culmination of many underlying mechanisms. Obesity is characterized as uncontrolled adipose tissue mass in the body and recognized as the fastest growing metabolic disorder in the world. An increase in adipose tissue mass can be the result of the production of new fat cells through the process of adipogenesis and/or the deposition of increased amounts of cytoplasmic triglyceride or lipid droplets per cell. In the adipogenesis process, proliferation of preadipocytes or precursor fat cells needs to be followed by the differentiation of these cells to the mature adipocyte phenotype. Increased lipid accumulation in the mature adipocyte cells is the most important feature of obesity disorder. Peroxisome Proliferator-Activator Receptor gamma (PPAR-y) is predominantly expressed in adipocytes and is a key determination factor for adipogenesis.

Fat is stored as triglycerides form in adipose tissue. The breakdown of this fat in fat cells into glycerol and fatty acids is known as lipolysis. During this process, free fatty acids are released into the bloodstream and circulate throughout the body. The hormones such as epinephrine, norepinephrine, glucagon and adrenocorticotropic hormone induce lipolysis. These hormones trigger 7TM receptors, which activate adenylate cyclase. This results in increased production of cAMP, which activates protein kinase A. Protein kinase A subsequently activates lipases found in adipose tissue. It is known that PPAR alpha plays an important role in regulating lipolysis through the control of lipid metabolic enzymes such lipoprotein lipase (LPL). (Ziuozenkova et al., PNAS, Mar. 4, 2003, Vol. 100, no. 5, 2730-2735).

Reducing the formation of new adipose tissue and formation of fat reserves through inhibition of differentiation of pre-adipocytes into mature adipocytes may be a good strategy to control adipogenesis mediated diseases, especially obesity. Modulation of adipogenesis and lipolysis in humans may thus lead to a reduction in the burden of obesity.

The body's adrenergic system plays a major part in regulating energy expenditure and lipolysis. In this process catecholamines mobilize energy-rich lipids by stimulating lipolysis in fat cells and thermogenesis in brown adipose tissue and skeletal muscle. The adrenergic receptor 3 is the principal receptor mediating catecholamine-stimulated thermogenesis in brown adipose tissue, which in humans is distributed about the great vessels in the thorax and abdomen (Thomas, G N, International Journal of Obesity, 545-551, 24, 2000). The 3-adrenergic receptor is also important in mediating the stimulation of lipolysis by catecholamines in the white fat cells of several species, including humans. The brown adipose tissue differs from white adipose tissue in that it has large numbers of mitochondria containing a so-called uncoupling protein, which can stimulate oxidative phosphorylation and thereby increase the metabolic rate (Peter Arner, The β3-Adrenergic Receptor—A Cause and Cure of Obesity? The New England Journal of Medicine, 333: p 382-383). The role of brown adipose tissue is to oxidize lipids to produce heat and rid the body of excess fat. White adipose tissue, which includes subcutaneous and visceral adipose tissue, is much more abundant. It serves to store fat, which can be mobilized by lipolysis to generate free fatty acids for use by other tissues.

Selective agonists of 3-adrenergic receptors are potentially useful in treating obesity because they could enhance energy expenditure with few 1- or 2-adrenergic side effects. A number of 3-adrenergic agonists have been developed and tested experimentally. Hence the treatment with β3-selective agonists can markedly increase energy expenditure and decreases obesity.

Low caloric diets with or without exercise can help with temporary weight loss; however, diet and exercise alone have not proven successful for long-term solutions in weight management (H. G. Preuss, et al., Nutrition Research, 2004, 24, 45-48). In addition, supplementation with drugs that suppress appetite, reduce food intake, reduce dietary fat absorption, increase energy expenditure and effect nutrient partitioning or metabolism have potential efficacy but they are unfortunately accompanied by adverse side effects (C. A. Haller and N. L. Benowitz., New England J. Medicine, 2000, 343, 1833-1838). The pharmaceutical drug, such as phentermine (Fastin, Adipex P), is prescribed for weight control but these have side effects like high blood pressure, headache, insomnia, irritability and nervousness. The other important drugs for weight control are Xenical (Roche Pharm. Co. Ltd., Swiss) and Reductil (Abbot Co. Ltd., USA), which cause gas generation, cramps, diarrhea and elevated blood pressure, common side effects. All these therapies are based on active ingredients that are of synthetic origin.

Effective anti-obese therapies with satisfactory efficacy and acceptable safety have been long overdue. More importantly, anti-obese agents of natural origin with proven safety are greatly needed to control the growing menace. Many herbal and natural products containing gymnema extract, *garcinia* extract, or carnitine, for example are known to prevent fat accumulation through the inhibition of fat absorption, enhancement of fat decomposition, and the enhancement of fat consumption by the body. It is particularly advantageous for inhibition, amelioration and prevention of obesity if an anti-obesity action can be imparted to food products and beverages, which are ordinarily ingested.

The *Piper betle* plant is a Piperaceae plant indigenous throughout the Indian Malay region. It is also being cultivated in Madagascar, Bourbon and the West Indies. It is a climbing shrub trained on poles or tall trees as a branching vine. It is generally too tender to grow outside of the tropics.

*Piper betle* has thousands of years of history in traditional Ayurvedic medicine as treatment for diabetes, cough, digestion and many other ailments (Glossary of Indian Medicinal Plants, pp. 195, 1996). In Indian Subcontinent and East Asian countries Betel leaf is regularly ingested as paan, a popular after meal digestive. The paan is a parcel of Betel leaf wrapped around a mixture of fragrant spices, slaked lime fine shreds of areca nut. Betel leaf and areca nut chewing is a tradition which dates back to thousands of years and the habit has been passed down through the generations and now provides a culture link to their past. Betel leaf and slaked areca nut are commonly used in marriage functions and other important ceremonies in India. Chewing of Betel leaves is also suggested as a remedy for catarrhal and pulmonary disorders.

The chief constituent of the betel leaves is a volatile oil. It mainly produces many phenolic metabolites, called chavibetol, chavicol, hydroxychavicol and eugenol. The inflorescence of *Piper betle* contains high concentrations (15 mg/g fresh weight) of safrole, an essential oil used in cosmetics and as a food flavoring agent.

Hydroxychavicol suppressed the growth of KB cells in cell media and resulted in cell cycle arrest at late Sand G2/M phase of the cell cycle and induces apoptosis. The *Piper betle* leaf extract showed protective effect from alcoholic toxicity in the rat brain and ameliorate hepatic marker enzymes and tissue antioxidant status in ethanol-treated Wistar rats (Saravanan R, et. al.; J. Med Food 6:261-265). *Piper betle* extract showed the ability to scavenge the free radicals involved in initiation and propagation steps of cancer. It exhibited potent antioxidant activity (Rathee J S, et. al.; J Agric Food Chem. 2006; 54(24):9046-54). Ethanolic extract of *Piper betle* exhibited radio protective property (Bhattacharya, S., et. al., J. Radiation Research, 46(2), 165-171, 2005).

Arambewel et al., showed significant reduction of blood glucose level with oral administration of *Piper betle* extracts (J. Ethanopharmacology, 102, 239-245, 2005). Oral administration of leaf suspension for 30 days to STZ diabetes rats resulted in significant reduction in blood glucose, glycosylated hemoglobin, decreased activities of liver glucose-6-phosphate and fructose-1,6-bisphosphatase with a concomitant increase in liver hexokinase (Santha Kumar et. al., 1. Medicinal food, 9, 108-112, 2006). Oral administration of 300 mg betel extract per day to rats showed significant hypolipidemic effect (Pharmaceutical biology, 42, 323-327, 2004).

U.S. Pat. No. 6,531,166 describes the effect of Betel leaf water extract on the enhancement of cellular immune response mediated by Th1 helper T-Iymphocytes.

U.S. Pat. No. 6,967,034 describe a new herbal-based composition and method for treatment of CD33+ acute and chronic myeloid leukemia by *Piper betle* leaf extracts, and to provide a process for the isolation of active fraction from leaves or any other plant parts of *Piper betle* to treat CD33+ AML and CML with a simplified method of isolation of active components from all plant parts of *Piper betle* possessing biological activities relevant to the treatment of CD33+ AML and CML.

U.S. Pat. No. 6,531,115 provides an analgesic and refreshing herbal composition useful as dentrifices, said composition comprising 50-60% wt. of Betel extract (from *Piper betle* leaves); of one or more group I essential oil selected from *Levender officinal*, Dementholised oil (ex-*Mentha arvensis*), Fennel oil and *Ocimum gratissimum*; one or more group II essential oils and their isolates selected from *Ocimum Sanctum*, Pulegone (ex. *Mentha pulegonium*), Carvone (ex. Dill seed) and Menthol (ex. *Mentha arvensis*); one or more group III essential oils selected from Camphor, turpentine oil, Cedarwood oil and Safrole oil, along with Thymol and preservative/antioxidant, and a process for preparing the composition.

U.S. Pat. No. 7,045,157 describes process of preparation and the use of betel leaf extract to induce IFNγ from human peripheral blood mononuclear cells and as a Th1 type immune modulator.

U.S. Pat. No. 6,413,553 describe a pharmaceutical formulation for blocking 5-lipoxygenase activity, which is useful as a leukotriene synthesis and IL4 inhibitor and as a Th1 immunomodulator comprising an effective amount of a combination of aqueous extracts and lyophilized extracts of *Piper betle* and *Murrya koeniggii*, and a method of treating humans for respiratory conditions.

U.S. Pat. No. 6,610,332 relates to method of treating visceral leishmaniasis or kala-azar by administering effective amount of betel leaf extract or lyophilized extract together with or associated with an additive and a composition comprising betel leaf extract with a pharmaceutically acceptable additive.

JPH130685A2 describe an antiallergic agent obtained by formulating an extract extracted with water or an organic solvent from leaves of *Piper betle* L. and demethyleugenol isolated and purified from the extract as active ingredients.

JP2000290165A2 describes a skin aging inhibitor containing as an active ingredient, the solvent extract of at least one plant selected from the group consisting of *Pipturus argenteus* (Forst.f.) (Indonesian name: Trembesi), *Phyllanthus pulcher* (Baill.) M.A. (Indonesian name: Naga buana) and *Piper betle* L. (Indonesian name: Daunsirih), especially the leaves, stems and barks of the *Pipturus argenteus* (Forst.f) (Indonesian name: Trembesi), the leaves of the *Phyllanthus pulcher* (Baill.) M.A. (Indonesian name: Naga buana), and the leaves, whole plant, stems and fruits of the *Piper betle* L. (Indonesian name: Daunsirih). The skin aging inhibitor is formulated to cosmetics, medicines, quasi drugs, foods and the like to utilize the excellent skin aging-inhibiting action.

U.S. Pat. No. 5,698,199 describes lipolysis acceleration method, which comprises orally administering a thistle-series or pepper-family plant or an extract thereof; or dermatologically applying it by local administration or as a bath medicine composition. The inventors describe the lipolysis activity of *Piper nigrum* and *Piper longum*. However, the anti-adipogenic or lypolysis activity of *Piper betle* has not been investigated/disclosed by the inventors.

WO06068777A3 and the equivalent US patent US2006134231 describe topical compositions comprising at least one plant extract selected from the group consisting of *Rhinacanthus nasutus, Humulus scandens, Sesbania grandiflora, Amorphophallus campanulatu, Pouzolzia pentandra,* and *Piper betle* and any combinations thereof useful in treating, preventing, ameliorating, reducing and/or eliminating loss of subcutaneous fat in the skin. However, the above application does not mention the treatment for visceral fat. Visceral fat is composed of several adipose depots including mesenteric, epididymal white adipose tissue (EWAT) and perirenal depots. Visceral fat accumulation is associated with increased risk of heart disease and type 2 diabetes.

Similarly none of the other patents, listed above, encompassed the anti-adipogenic activity and lipid accumulation inhibition activities of *Piper betle*. Therefore, the present inventors have investigated the anti-adipogenic activity of *Piper betle* extracts and its compositions whose target site of action being visceral fat.

The small twining creeper *Dolichos biflorus*, popularly known as horse gram, belongs to Papilionaceae family. The small, grayish brown and flattened seeds are called vulavalu in vernacular language in the state of Andhra Pradesh, India. Horse gram is native to most parts of India, and is found at an altitude of about 1000 meters. It has value both as food and fodder. The cooked whole seeds or sprouts of horse gram are consumed by a large population in rural areas of Southern India. A popular regional delicacy made of horse gram in Andhra Pradesh is called vulava charu. *Dolichos* is described as a herb of mildly heat producing nature. The composition containing *dolichos*, astragalus, codonopsis, rehmannia, and tortoise shell is used for countering the immune suppression in cancer patients. According to the Oriental Materia Medica, *dolichos* is also useful for "alcohol intoxication." In ethnobotany and as a home remedy, it has application for urolithiasis, dysuria, bleeding piles. In patients with oedema, a diuretic effect has been shown. As a home remedy, it has also been used in vaginal bleeding, epistaxis and leucorrhoea. In dysuria, its action is due to its diuretic property. It is also used to reduce crystalluria and to lyse stones. The powdered seeds are used as a poultice to induce sweating.

The administration of *D. biflorus* to experimental rabbits manifested protection against high fat diet (HFP) induced oxidative stress in different tissues. (Muthu, A K, et. al., Indian J. Pharmacol., 38(2): 131-132, 2006). It also showed lipid lowering effect in experimental rats (Muthu A K, et al., Indian J. Expt. Biol. 43; 522-525, 2005). U.S. Pat. No. 5,916, 567 describes an herbal anti-diabetic therapeutic product comprising powdered inner seed of *Dolichos biflorus* and also the powdered fibrous outer shell of the seed of *Dolichos biflorus* wherein the product is subjected to radiation for a period of 10-20 minutes.

However, none of the prior art reported or disclosed the anti-adipogenic or lipid accumulation inhibition activity of the extracts or purified fractions derived from the *Dolichos biflorus* plant, more specifically its application for adipogenesis mediated disorders was not encompassed by the literature.

A selected combination of *Piper betle* and *Dolichos biflorus*, for example imparts complementary, but largely separate mechanisms of action in the body. While not wishing to be bound by theory, applicant submits that the benefits of combining the *Piper betle* and *Dolichos biflorus* extracts, that has unexpectedly showed synergetic effects, are due, at least in part, to the multiple modes of activity of the composition. The antiadipogenic and pro-lipolytic activities of *Dolichos biflorus* in combination with antiadipogenic activity of *Piper betle* offer an effective combination to combat obesity.

It is therefore becomes an object of the present invention to develop herbal compositions for the prevention, maintenance and control of obesity.

OBJECTS OF THE PRESENT INVENTION

A main object of the present invention is to provide a novel synergistic herbal composition having high safety and a potent anti-adipogenic action for inhibition, amelioration and prevention of adipogenesis mediated diseases, and a method of inhibiting or preventing adipogenesis involved diseases.

Another object of the present invention is to provide the process for the extraction of the dried plant parts of *Piper betle* and *Dolichos biflorus* using water or organic solvents alone or the mixtures thereof.

Yet another object of the present invention is to develop a composition containing the biologically active ingredient capable of reducing body weight, total serum cholesterol level, phospholipids and triglycerides useful for the inhibition of adipogenesis mediated diseases which helps in keeping slim.

Still further object of the present invention is to provide a novel anti-adipogenic herbal formulation useful as a weight loss drug in the treatment of obesity and used in atherosclerosis.

Still another objective of the present invention is to provide herbal formulation(s) that reduces serum cholesterol, phospholipids and triglycerides.

Still another object of the present invention is to provide herbal formulation(s) in combination with other anti-adipogenic plants extracts or powders useful in lowering lipid per oxidation, hyperlipidemia and used for the treatment of atherosclerosis.

SUMMARY OF THE INVENTION

Accordingly, to meet the above stated objectives, the present invention discloses herbal anti-adipogenic composition for inhibiting adipogenesis and/or in promoting body weight loss and/or stimulating thermogenesis, comprising, biologically effective amount of extracts or purified fractions derived from *Piper betle* in combination with one or more of the extracts or fractions derived from *Dolichos biflorus, Commiphora mukul, Boerhaavia diffusa, Tribulus terrestris* and

*Zingiber officinale*, and optionally containing a bioenhancing agent or a bio-protecting agent.

The composition of the invention optionally comprises one or more of the other known antiobese ingredients or anti-inflammatory agents or anti-oxidant agents or anti-diabetic agents or adaptogen(s), along with biologically acceptable carrier or diluents. In accordance to the present invention, dried plant parts of *Piper betle* and *Dolichos biflorus*, including leaves, stems, flowers, roots, berries, seeds alone or in combination, are extracted individually with water or C1 to C3 alcoholic solvents or their mixers thereof. The respective extracts are combined, filtered and dried under vacuum separately to obtain residue.

In one aspect, the extracts/purified fractions of *Piper betle* and/or *Dolichos biflorus* comprising the active ingredient is formulated into a solid, semi-solid or liquid dosage form suitable for oral and parenteral administration alone or in combination with one or more of known anti-adipogenic agents. In another aspect, the extracts/purified fractions of *Piper betle* and/or *Dolichos biflorus* comprising the active ingredient are formulated into nutraceuticals and diet supplements including food and beverages.

In a further aspect, the extracts/purified fractions of *Piper betle* is formulated with one or more plant extracts selected from the group comprising of *Commiphora mukul*, *Boerhaavia diffusa*, *Tribulus terrestris* and *Zingiber officinale*, and optionally a bioenhancing agent or a bio-protecting agent useful in the treatment of adipogenesis mediated diseases.

The present invention also discloses methods for preventing and controlling adipogenesis mediated diseases, and methods of administration of the said extracts or purified fractions of *Piper betle* or *Dolichos biflorus* or a combination of both as such or in the form of formulated dosage compositions, particularly effective for inhibition, amelioration or prevention of various diseases caused by compromised adipogenesis and lipolysis thereof, for example, obesity, lipid storage disease, hyperlipemia and hypercholesterolemia.

DETAILED DESCRIPTION OF THE INVENTION

Figure 1:
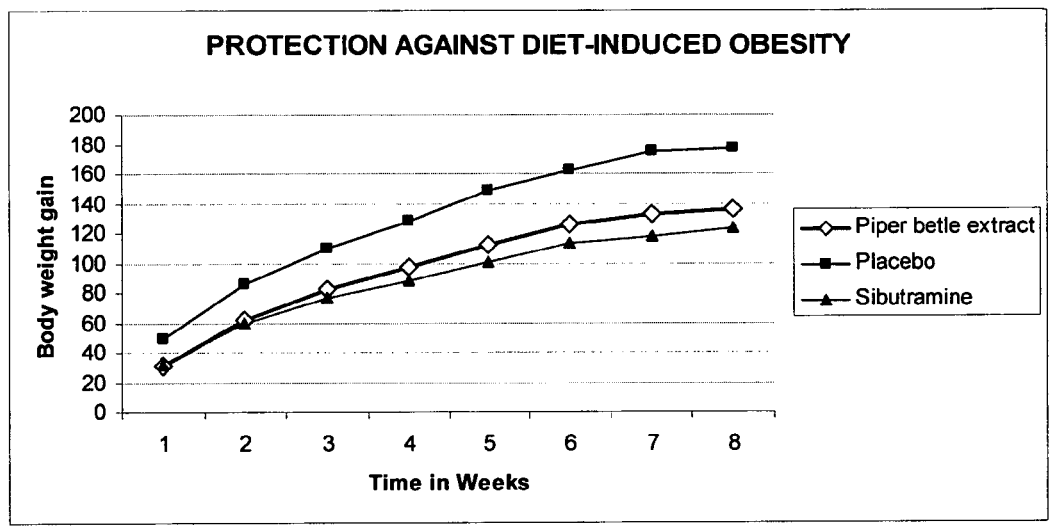
FIG. 1 presents protective antiobese activity of *Piper betle* (250 mg/kg body weight) against diet induced obesity.

In the adipogenesis process, proliferation of preadipocytes needs to be followed by the differentiation of these cells to the mature adipocyte phenotype. Increased lipid accumulation in the mature adipocyte cells is the most important feature of this maturation process.

The uncontrolled fat accumulation in the body during the metabolic process is predominantly driven by the following key events. 1). Over expression and increased activity of Protein Tyrosine Phosphatase IB during the differentiation process of preadipocytes to mature adipocytes, 2). Highly increased lipid accumulation was noted in the differentiated mature adipocytes, 3). Over expression and increased activity of Peroxisome Proliferator-Activated Receptor-gamma (PPAR-γ) a ligand activated nuclear receptor that acts as a lipid sensor, integrating the homeostatic control of energy, lipid, and glucose metabolism.

Thermogenesis is a metabolic process in which calories consumed and stored as fat by the body are expended to dissipate energy as a heat. This metabolic process primarily occurs in adipocytes, such as brown adipose tissue. Stimulation of thermogenesis causes fat cells to burn energy and a consequence of this can be loss of body weight.

Based on the above information, inventors of the present invention have undertaken screening strategy of many plant extracts using in vitro cell based experimental protocols followed by in vivo experimental studies and found that extracts or fractions of *Piper betle* and *Dolichos biflorus* exhibit potent anti-adipogenic action by inhibiting lipid accumulation in vitro. In addition, many other plant extracts such as, *Commiphora mukul*, *Boerhaavia diffusa*, *Tribulus terrestris*, *Zingiber officinale* also showed significant anti-adipogenic activity, which have been included in the present invention.

*Piper betle* hydroalcohol extract and some of its compositions with the about antiadipogenic extracts were tested for their protective efficacy and therapeutic efficacy against diet induced obesity in Sprague-Dawley rats. These extracts and composition conferred significant protection from weight gain in diet induced obese animals. They have also shown therapeutic efficacy against diet induced obesity.

In a preferred embodiment, the extract/purified fraction of *Piper betle* and/or *Dolichos biflorus* comprising the active ingredient is formulated into a solid, semi-solid or liquid dosage form suitable for oral and parenteral administration. Different compositions have been prepared with variable concentrations of *Piper betle* and *Dolichos biflorus* and evaluated for their anti-adipogenic property and anti-obese activity. These compositions have shown good anti-adipogenic and anti-obese activity both in vitro and in vivo.

In another preferred embodiment, the combination of *Piper betle* with one or more of *Commiphora mukul*, *Boerhaavia diffusa*, *Tribulus terrestris*, *Zingiber officinale* along with bio-enriching and bio-protectant agents were evaluated and found to show good anti-adipogenic and anti-obese activity. *Piper betle* in combination of *Commiphora mukul*, *Boerhaavia diffusa*, *Tribulus terrestris*, and *Zingiber officinale* along with *Piper nigrum* extract as a bio-enriching agent also showed significant anti-adipogenic activity in vitro and anti-obese activity in vivo.

Adipose tissue is the primary source of circulating leptin and as the adipose tissue mass increases more leptin is produced in obese people. In controlled condition, it was proved that higher levels of adiposity were associated with high concentration of serum leptin. Thus the circulating leptin appears to be one of the best biological markers of obesity and that hyper leptinemia is closely associated with several metabolic disorders.

Therefore, the inventors further investigated the serum leptin levels in the treatment group. The significant reduction in serum leptin levels observed in the treatment group of animals supplemented with anti-adipogenic products of the present invention compared to the mean leptin level of controlled group may be taken as a measure of reduction in the visceral fat tissue mass and an additional indicator for the efficacy of therapeutic agent.

In another preferred embodiment, the extracts or purified fractions from *Piper betle* individually or as said compositions may further comprise anti-adipogenic or anti-obese agents selected from *Holoptelia integrifolia* extracts, *Garcinia combogia* extract, green tea extract, green coffee bean extract, eucalyptus plant extract, bitter orange (*Citrus aurantium*) extract, Conjugated linoleic acid, *Hoodia Gordonii* extract, *Allium sativa* extract, chromium (III) complexes, DHEA, 7-Keto-DHEA.

In a further variation of the invention the compositions containing *Piper betle* and *Dolichos biflorus, Commiphora mukul, Boerhaavia diffusa, Tribulus terrestris, Zingiber officinale* along with a bio-enriching agent *Piper nigrum* extract may be supplemented with one or more complimentary therapeutic herbal or pharmaceutically derived active ingredients. A list of suitable ingredients that are included for this auxiliary addition include, but are not limited to, those having stimulatory or metabolism increasing properties, blood pressure and/or cholesterol reducing effects, the ability to counteract insulin resistance, anti-oxidants and anti-inflammatory agents, anti-diabetic agents, adaptogens, especially bio-protectants like *Curcuma longa* and bio-enhancers like *Piper nigrum* or *Piper longum* etc.

Effective amounts of these compositions can be formulated with or without carriers or additives that are approved for human consumption and administered to mammals.

The herbs of the inventive composition are identified by their botanical characteristics, as well as by the chemical compounds contained within the plant that may be extracted by chemical manufacturing processes. These phytochemical constituents or purified fractions or functional equivalents derived from the herbs that mimic, individually or collectively, the effect of the herbs and herbal extracts may be substituted in place of herb without departing from the spirit and utility of the invention.

Moreover, the compositions of *Piper betle* with *Dolichos biflorus* or other ingredients of the present invention can be combined with ordinary foods to impart weight control capabilities to the modified foods. For example, the compositions can be mixed with soft drinks, food supplements, candy, or high-energy bars, and virtually any other food that can be supplemented with a powder or liquid. Thus, the invention specifically includes food substances of specific types combined with the composition of the invention in specified forms and quantities.

The raw materials for the purposes described in the present invention can be selected from the whole plant or any effective part including leaves, stems, flowers, roots, berries, flowers, seeds or part combination thereof. The preferred part of *Piper betle* is leaf and for *Dolichos biflorus* the effective plant part is seed. The preferred part for *Commiphora mukul* is gum material, *Boerhaavia diffusa* is whole herb, *Tribulus terrestris* is fruit, *Zingiber officinale* is rhizome and for *Piper nigrum* the preferred part is fruit. The form of the herb used for the invention can be in any form, which is effective including, but not limited to, dry powders, grounds, emulsions, extracts, purified fractions.

The solvent for the extraction of herbs of the invention is selected from water or organic solvent or mixed solutions thereof. Examples of the organic solvent include polar organic solvents such as lower alcohols having 1 to 4 carbon atoms such as methanol, ethanol, propanol, isopropanol, n-butanol, isobutanol, sec-butanol, tert-butanol and the like, and ketones such as dimethyl ketone, methyl ethyl ketone, acetone, methyl isobutyl ketone and the like; and non-polar organic solvents such as methyl acetate, ethyl acetate, butyl acetate, diethyl ether and the like. These polar organic solvents and non-polar organic solvents can also be used in appropriate combination, preferably 40-60% methanol. The preferred solvent for *Dolichos biflorus* is methanol or ethanol, whereas the preferred extraction solvent for *Piper betle, Boerhaavia diffusa, Tribulus terrestris, Zingiber officinale* and *Piper nigrum* is 60% methanol.

The effective amounts of the ingredients, individually or in compositions can be effective to suppress adipogenesis, stimulate thermogenesis, promote weight loss, inhibit the weight gain. An "effective amount" indicates an amount needed to achieve the purpose for which it is administered. The *Piper betle* as an individual ingredient or in a composition comprises an amount which is effective for the stated purpose.

In preferred aspects of the invention, the novel compositions contain specific combinations of at least *Piper betle* and other ingredients. Other beneficial herbal ingredients or pharmaceutically acceptable ingredients will be additional and separate from the ratios provided herein for the two principal herbal ingredients. The *Piper betle* and *Dolichos biflorus* composition, for example, comprise *Piper betle* extract in the range of 1%-99% by weight and *Dolichos biflorus* extract in the range of 0%-70% by weight. Another preferable composition of *Piper betle* comprises *Piper betle* extract in the range of 10-40%, *Commiphora mukul* extract in the range of 10-40%, *Boerhaavia diffusa* extract in the range of 10-40%, *Tribulus terrestris* extract in the range of 10-40%, *Zingiber officinale* extract in the range of 10-40% and the bio-enhancer *Piper nigrum* extract in the range of 10-40%.

To obtain full benefit of composition of the present invention, it is preferable that the above-mentioned *Piper betle* ingredient itself or the compositions are used as such, or the active ingredient is formulated into a solid, semi-solid or liquid dosage or *Dolichos biflorus* or combination thereof or their compositions are used as such or the active is formulated into specific forms such as solid, semi-solid or liquid dosage by adding a conventional biologically acceptable carrier or diluent.

The pharmaceutical specific form includes, for example, oral agents such as tablets, soft capsule, hard capsule, pills, granules, powders, emulsions, suspensions, syrups, and pellets; and parenteral agents such as injections, drops, suppositories and the like by methods known per se.

In another aspect of the invention, the compositions comprising extracts, purified fractions or dry powder of *Piper betle* and/or *Dolichos biflorus* of the present invention are in the form of a dietary formulations such as a healthy food or food for specified health uses such as solid food like chocolate or nutritional bars, semisolid food like cream or jam, or gel and also beverage and the like, such as refreshing beverage, coffee, tea, milk-contained beverage, lactic acid bacteria beverage, drop, candy, chewing gum, chocolate, gummy candy, yoghurt, ice cream, pudding, soft adzuki-bean jelly, jelly, cookie and the like.

The examples of the biologically acceptable carrier or diluents employed in the present invention includes, but are not limited to, surfactants, excipients, binders, disintegrators, lubricants, preservatives, stabilizers, buffers, suspensions and drug delivery systems.

Preferred examples of solid carriers include, glucose, fructose, sucrose, maltose, sorbitol, stevioside, corn syrup, lactose, citric acid, tartaric acid, malic acid, succinic acid, lactic acid, L-ascorbic acid, dl-α-tocopherol, glycerin, propylene glycol, glycerin fatty ester, polyglycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors, and preservatives.

Preferred examples of liquid carriers (diluents) includes, distilled water, saline, aqueous glucose solution, alcohol (e.g. ethanol), propylene glycol, and polyethylene glycol; and oily carriers such as various animal and vegetable oils, white soft paraffin, paraffin, and wax.

In a most preferred aspect of the invention, the method of treatment includes, administering an effective amount of *Piper betle* or *Dolichos biflorus* or combination thereof or their compositions, as described herein to a mammal in need thereof, where the amount varies depending on the nature of the formulation and suggested human or animal dosage of the extract or the fractions.

The compositions of the present invention will be administered at least once a day, preferably twice a day. Alternatively, the compositions can be administered as part of a weight controlling or other treatment regimen and be administered either before meals or as a meal replacement such as a milk-shake or any other beverage. It is also contemplated that the compositions will be included as part of snack bars or other processed foods as part of an overall weight control plan.

In alternative aspects of the invention, the compositions of the present invention are delivered as part of controlled release tablets, designed for once daily administration. Such formulations are made using well known techniques using controlled release polymer-based coatings, liposomal delivery targets or nanoparticles.

In an embodiment of the invention, when the mammal in need of the inventive composition is an animal, the feed is prepared by mixing the inventive composition with various components used in the animal feed for the purpose of inhibition, amelioration or prevention of adipogenesis mediated diseases such as obesity, lipid storage disease, hyperlipemia, arteriosclerosis and thrombosis, or for the purpose of inhibition or reduction of an amount of triglyceride or an amount of cholesterol in blood or preventing obesity.

Based on the above information, several in vitro cellular and molecular biology experiments were carried out to accomplish the objects described above by focusing on some underlying mechanisms of obesity.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Dried leaves of the plant material *Piper betle* (1 Kg) were pulverized to coarse powder, extracted with methyl alcohol (5 L) at RT for 1 hr. Extraction process was repeated thrice using methyl alcohol (3 L+3 L+2 L). All the extracts were combined, the combined alcohol extracts were fine filtered, and the clear extract was evaporated to dryness on a climbing film evaporator at 50-60° C. under vacuum to obtain the residue (81 g).

Example 2

Dried leaves of the plant material *Piper betle* (1 Kg) were pulverized to coarse powder, extracted with 60% methanol (6 L) at RT for I hr. Extraction process was repeated three times using 60% methanol (5 L+3 L+3 L). All the hydroalcohol extracts were combined, subjected to fine filtration, and the clear extract was evaporated to dryness on a climbing film evaporator at 50-60° C. under vacuum to obtain the residue (110 g).

Example 3

Dried leaves of the plant material *Piper betle* (1 Kg) were pulverized to coarse powder, extracted with water (6 L) at RT for I hr. Extraction process was repeated three times using water (4 L+4 L+2 L). All the extracts were combined, the combined aqueous extracts were fine filtered, and the clear extract was evaporated to dryness on a climbing film evaporator at 50-60° C. under vacuum to obtain the residue (120 g).

Example 4

Dried leaves of the plant material *Dolichos biflorus* (1 Kg) was pulverized to coarse powder, extracted with methanol (6 L) at RT for 1 hr. Extraction process was repeated three times using 60% methanol (5 L+3 L+3 L). All the alcohol extracts were combined, subjected to fine filtration, and the clear extract was evaporated to dryness on a climbing film evaporator at 50-60° C. under vacuum to obtain the residue (145 g).

Example 5

Composition 1: A composition was prepared by mixing unit doses of the following components:

| | |
|---|---|
| *Piper betle* 60% methanol extract | 1 g |
| *Dolichos biflorus* methanol extract | 1 g |

Example 6

Composition 2: A composition was prepared by mixing unit doses of the following components:

| | |
|---|---|
| *Piper betle* 60% methanol extract | 1 g |
| *Dolichos biflorus* methanol extract | 2 g |

Example 7

Composition 3: A composition was prepared by mixing unit doses of the following components:

| | |
|---|---|
| *Piper betle* 60% methanol extract | 2 g |
| *Dolichos biflorus* methanol extract | 1 g |

Example 8

Composition 4: A composition was prepared by mixing unit doses of the following antiadipogenic extracts along with a bio-enhancer *Piper nigrum* extract:

| | |
|---|---|
| *Piper betle* 60% methanol extract | 1 g |
| *Commiphora mukul* 60% methanol extract | 1 g |
| *Boerhaavia diffusa* 60% methanol extract | 1 g |
| *Tribulus terrestris* 60% methanol extract | 1 g |
| *Zingiber officinale* 60% methanol extract | 1 g |
| *Piper nigrum* 60% methanol extract | 1 g |

Example 9

Composition 5: A composition was prepared by mixing unit doses of the following compounds:

| | |
|---|---|
| *Piper betle* 60% methanol extract | 99.9 g |
| Colloidal silicon dioxide (aerosol) | 0.1 g |

Example 10

Assessment of Inhibition of Lipid Accumulation in Differentiated Adipocytes by *Piper betle* and Other Herbal Extracts, and their Compositions One hundred thousand 3T3-L1 Human pre-adipocyte cells in Dulbecco's Modified Eagles Medium (DMEM) containing 10% Fetal Bovine Serum (FBS) were taken into each well of a 24-well plate and incubated for 48 h at 37° C. and 5% C02. The differentiation of preadipocytes cells was initiated in a differentiation medium containing 10 µg/ml insulin, 1.0 µM dexamethasone, and 0.5 mM isobutylmethylxanthine (IBMX) for 48 h. After this the medium was replaced by DMEM containing 10 µg/ml insulin and incubated for 3 days. Then the differentiating cells were treated separately with 10 µg/ml of methanol extract of *Dolichos biflorus*, hydroalcohol (60% methanol) extracts of *Piper betle, Commiphora mukul, Boerhaavia diffusa, Tribulus terrestris, Zingiber officinale* and *Piper nigrum* or their compositions (compositions 1, 2, 3 and 4) and maintained in the medium for another 3-5 days. The cells incubated with 0.1% DMSO were considered as the vehicle control. After the incubation period, cells were washed with phosphate buffered saline (PBS) and fixed with 10% buffered formalin for 1 h at room temperature. One small aliquot of cell suspension was separated for cell counting in hemocytometer chamber. Fixed cells were stained with Oil Red 0 solution to measure the cellular neutral lipid accumulation. Briefly, cells were washed with PBS, fixed with 10% buffered formalin and stained with Oil Red 0 solution (0.5 g in 100 ml isopropanol) for 10 min. After removing the staining solution, the dye retained in the cells was eluted using isopropanol and OD was measured at 550 nm. The inhibition of fat accumulation in the treated cells was compared with the mock treated differentiated adipocytes. The treated cells and the control cells were also analyzed and compared for inhibition of lipid accumulation visually under microscope and recorded digitally in suitable image capture system. The % inhibition of lipid accumulation exhibited by individual ingredients and their compositions is summarized in Table 1.

TABLE 1

Anti-adipogenic activity of Betel extracts and compositions

| S. No. | Name of the product | % inhibition of lipid accumulation |
|---|---|---|
| 1 | *Dolichos biflorus* (A) | 42.3 |
| 2 | *Dolichos biflorus* (B) | 33.5 |
| 3 | *Piper betle* (A) | 19.2 |
| 4 | *Piper betle* (B) | 42.0 |
| 5 | Composition 1 | 48.0 |
| 6 | Composition 2 | 40.1 |
| 7 | Composition 3 | 44.0 |
| 8 | *Commiphora mukul* (B) | 35.6 |
| 9 | *Boerhaavia diffusa* (B) | 38.4 |
| 10 | *Tribulus terrestris* (B) | 36.9 |
| 11 | *Zingiber officinale* (B) | 29.6 |
| 12 | *Piper nigrum* (B) | 41.5 |
| 13 | Composition 4 | 51.8 |

A: methanol extract;
B: 60% methanol extract

Example 11

Protective Effect of *Piper betle* Against Diet Induced Obesity in Rats

Selected healthy Sprague-Dawley rats were randomly assigned to control or various treatment groups (n=6). All the animals allocated for protective phase of the study were on dietary intervention by feeding high fat diet ad libitum and the animals allocated to treatment groups were simultaneously given oral administration of 250 mg/kg *Piper betle* hydroalcohol extract per day in 10 mL of 0.5% CMC, using gastric tube for the entire 8 week study duration. The test animals of the control group were simultaneously given 10 ml/kg 0.5% CMC. The animals of positive control group were given 7 mg/kg sibutramine in 10 mL of 0.5% CMC. Food and water consumptions were recorded daily, body weights were recorded weekly and fasting blood samples were collected before initiation, after 4th week and 8th week (termination) of the study. The *Piper betle* treated group exhibited reduction in weight gain during the study duration (FIG. 1), manifesting its antiobesic protective effect against fat rich diet. The treatment groups corresponding to 250 mg/kg *Piper betle* extract and 7 mg/kg sibutramine showed 30.6% and 44.4% protection respectively in weight gain, in diet induced obesity, when compared with untreated control group. The animals of the treatment group also showed significant reduction in serum triglycerides and lipid profile (anti-hyperlipidemic activity). Upon administration of *Piper betle* alcohol extract for a period of 60 days, the level of triglyceride in the obese rats was reduced by 33%. The levels of serum cholesterol and LDL were reduced by 22% and 23% respectively, whereas the level of HDL was increased by 11%.

Example 12

Anti-Obese Activity of *Piper betle* in Diet Induced Obese Rats

Figure 2:
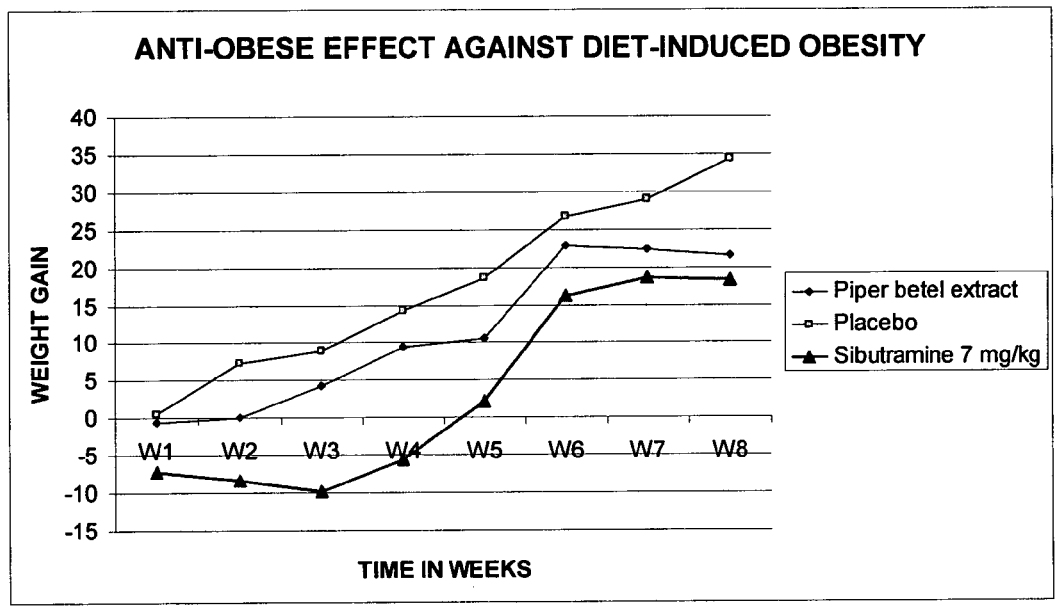
FIG. 2 presents antiobese activity of *Piper betle* extract (250 mg/kg body weight) against diet induced obesity.

Selected healthy Sprague-Dawley rats were randomly assigned for control or various treatment groups (n=6). All the animals allocated for the study were made obese through dietary intervention by feeding high fat diet ad libitum for 8 weeks. After 8 weeks, the treatment group of animals was given oral administration of 250 mg/kg of *Piper betle* 60% methanol extract per day in 10 mL of 0.5% CMC, using gastric tube for 8 week study duration. The control group of animals was given 10 ml/kg of 0.5% CMC. The animals of positive control group were given 7 mg/kg sibutramine per day in 10 mL of 0.5% CMC. Food and water consumptions were recorded daily, body weights were recorded weekly and fasting blood samples were collected before initiation, after $4^{th}$ week and $8^{th}$ week (termination) of the study. The *Piper betle* treated group exhibited reduction in weight gain during the study duration (FIG. 2), suggesting antiobese effect against diet induced obesity. The reduction in mean body weight gain of animals in treatment groups corresponding to 250 mg/kg *Piper betle* extract and sibutramine are about 59.2% and 87% respectively compared to those in the untreated control group. The treatment group of animals also showed significant reduction in serum triglycerides and lipid profile (anti-hyperlipidemic activity).

Example 13

Figure 3:
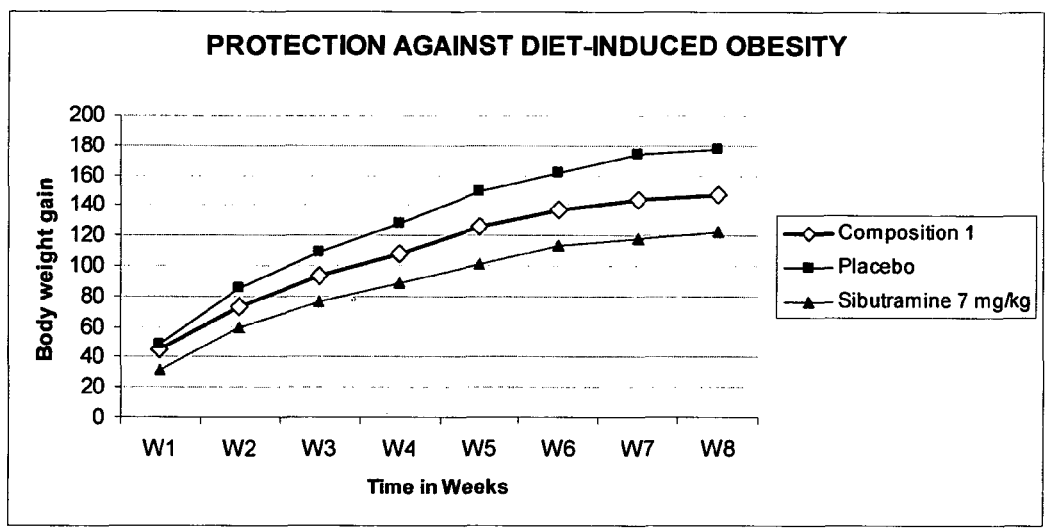
FIG. 3 presents protective antiobese activity of composition 1 [mixture of aqueous alcohol (methanol/water, 3:2) extracts of *Piper betle* and *Dolichos biflorus* (250 mg/kg body weight)] against diet induced obesity.

Protective Effect of Composition-1 (a Composition of Equal Unit Doses *Piper betle* 60% Alcohol Extract and *Dolichos biflorus* Methanol Extract) Against Diet Induced Obesity in Rats Selected healthy Sprague-Dawley rats were randomly assigned to control or various treatment groups (n=6). All the animals allocated for protective phase of the study were on dietary intervention by feeding high fat diet ad libitum and the animals allocated to treatment groups were simultaneously given oral administration of 250 mg/kg of composition-1 or 7 mg/kg sibutramine per day in 10 mL of 0.5% CMC, using gastric tube for the entire 8 week study duration. The test animals of the control group were simultaneously given 10 ml/kg 0.5% CMC. Food and water consumption were recorded daily, body weights were recorded weekly and fasting blood samples were collected before initiation, after $4^{th}$ week and $8^{th}$ week (termination) of the study. The treatment groups corresponding to composition-1 and sibutramine supplementation showed 20.7% and 44.4% reduction respectively in weight gain, against diet induced obesity, when compared with untreated control group (FIG. 3). The animals of the treatment group also showed significant reduction in serum triglycerides and lipid profile (antihyperlipidemic activity).

Example 14

Figure 4:
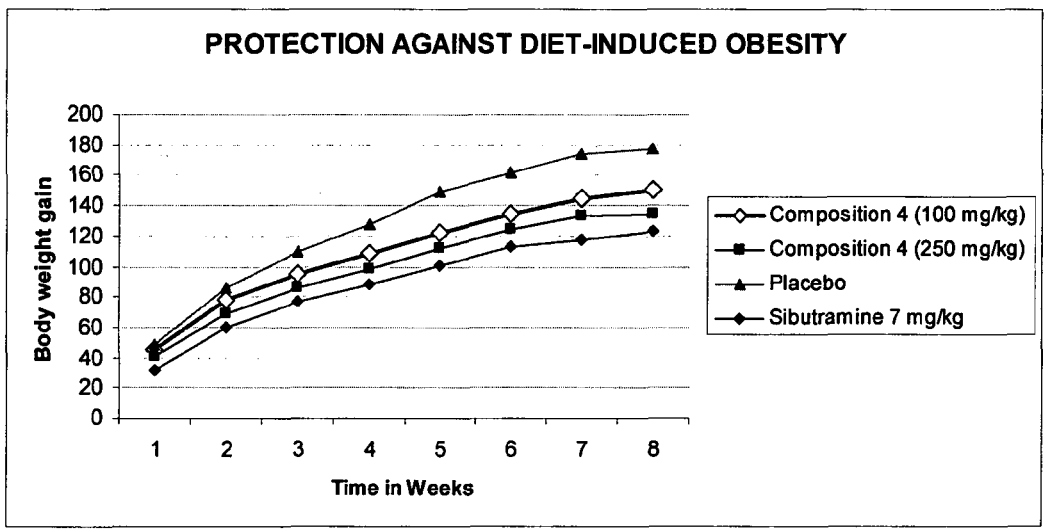
FIG. 4 presents protective antiobese activity of composition 4 [mixture of aqueous alcohol (methanol/water, 3:2) extracts of *Piper betle*, *Commiphora mukul*, *Boerhaavia diffusa*, *Tribulus terrestris*, *Zingiber officinale* along with a complimentary bio-enhancer, *Piper nigrum* (250 mg/kg body weight)] against diet induced obesity.

Protective Effect of Composition-4 (a Combination of Equal Unit Doses of 60% Methanol Extracts of *Piper betle*, *Commiphora Mukul*, *Boerhaavia Diffusa*, *Tribulus Terrestris*, *Zingiber Officinale* and *Piper nigrum*) Against Diet Induced Obesity in Rats Selected healthy Sprague-Dawley rats were randomly assigned to control or various treatment groups (n=6). All the animals allocated for protective phase of the study were on dietary intervention by feeding high fat diet ad libitum and the animals allocated to treatment groups were simultaneously given oral administration of 100 mg or 250 mg/kg of composition-4 or 7 mg/kg sibutramine per day in 10 mL of 0.5% CMC, using gastric tube for the entire 8 week study duration. The test animals of the control group were simultaneously given 10 ml/kg of 0.5% CMC. Food and water consumption were recorded daily, body weights were recorded weekly and fasting blood samples were collected before initiation, after $4^{th}$ week and $8^{th}$ week (termination) of the study. The treatment groups supplemented with 100 mg/kg and 250 mg/kg of composition-4 showed 18.4% and 24.3% reduction respectively in weight gain, against diet induced obesity, when compared with untreated control group (FIG. 4). The sibutramine supplemented treatment group showed 44.4% reduction in weight gain. The animals of the treatment group also showed significant reduction in serum triglycerides and lipid profile (antihyperlipidemic activity).

Example 15

Anti-Obese Activity of Composition 4 in Diet Induced Obese Rats

Figure 5:
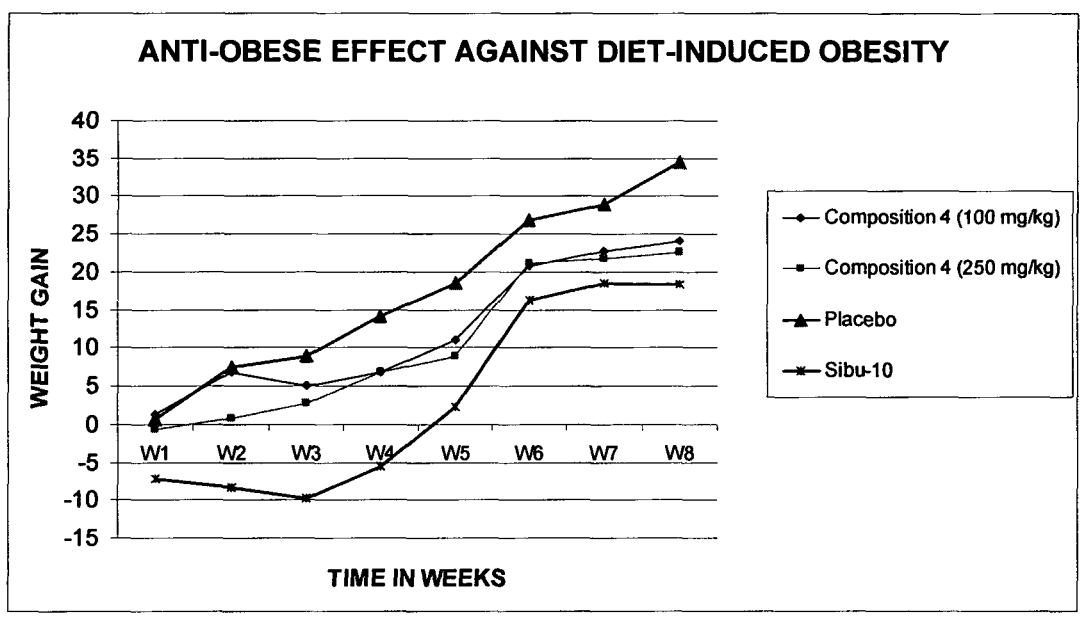
FIG. 5 presents antiobese activity of composition 4 [mixture of aqueous alcohol (methanol/water, 3:2) extracts of *Piper betle*, *Commiphora mukul*, *Boerhaavia diffusa*, *Tribulus terrestris*, *Zingiber officinale* along with a complimentary bio-enhancer *Piper nigrum* (250 mg/kg body weight)] against diet induced obesity.

Selected healthy Sprague-Dawley rats were randomly assigned to control or various treatment groups (n=6). All the animals allocated for the study were made obese through dietary intervention by feeding high fat diet ad libitum for 8 weeks. After 8 weeks, the treatment groups of animals were given oral administration of 100 mg or 250 mg/kg of composition-4 or 7 mg/kg sibutramine per day in 10 mL of 0.5% CMC, using gastric tube for 8 week study duration. The animals of control group were given 10 ml/kg of 0.5% CMC. Food and water consumption were recorded daily, body weights were recorded weekly and fasting blood samples were collected before initiation, after $4^{th}$ week and $8^{th}$ week (termination) of the study. The reduction in mean body weight gain of animals in treatment groups supplemented with 100 mg/kg and 250 mg/kg of composition-4 and sibutramine are 43.3%, 52.2% and 87%, respectively, compared to those in the untreated control group (FIG. 5). The treatment group of animals also showed significant reduction in serum triglycerides and lipid profile (anti-hyperlipidemic activity).

Example 16

Figure 6:
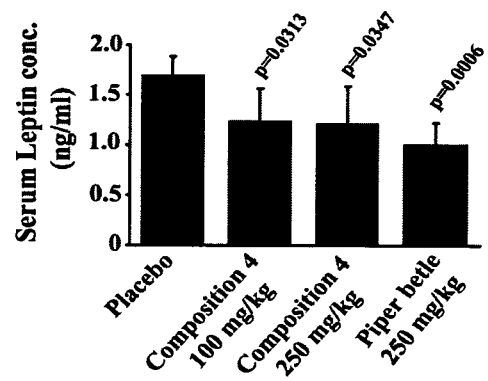
FIG. 6 presents bar diagrammatic representation of reduction of serum leptin concentrations (ng/ml) in protective (A) and therapeutic (B) efficacy evaluation of test compounds in diet induced obese rats. Each bar represents mean±SO of data obtained from 6 animals. Serum leptin level was measured by Rat Leptin ELISA kit. The P values are obtained from t-test, compared with the placebo group.
Figure 6:
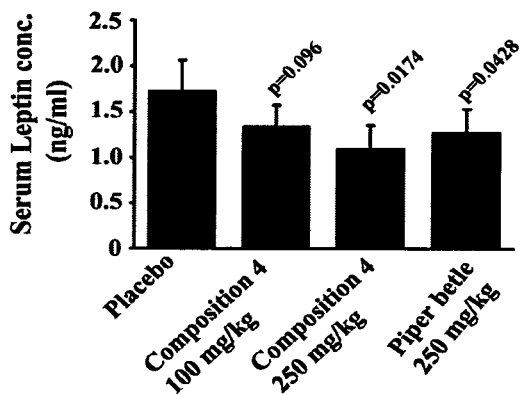

Effect of *Piper betle* Extract and Composition 4 on Serum Leptin Concentration in Diet Induced Obese Animals During the Protective Efficacy and Treatment Efficacy Evaluation Studies and Comparison with Leptin Level of Control Group of Animals Serum leptin concentration was quantitatively measured by a sandwich ELISA. The assay procedure was based on the instructions provided by the vendor (Linco Research, USA). The serum samples collected from treatment group of animals supplemented with *Piper betle* (example #s 11 and 12), composition 4 (example #s 14 and 15) and control group were selected and subjected to leptin analysis. Leptin present in the treatment group and control group rat serum samples was bound on the antiserum coated 96-well micro-titer plate. Biotinylated detection antibody was allowed to bind with the immobilized leptin and thereafter, horseradish peroxides enzyme was incubated to hind with the biotinylated conjugates. After washing away of the free enzyme the specifically bound enzyme activity was detected in presence of the substrate 3,3',5,5'-tetramethylbenzidene. The enzyme activity was measured spectrophotometrically at 450 nm. The concentration of leptin in the rat serum was measured by interpolation from a reference curve generated with the reference standards of known concentrations of rat leptin. The sensitivity of this assay is 0.04 ng/ml of leptin in rat serum. The mean serum leptin levels for different treatment groups supplemented with *Piper betle* (250 mg/kg, example #11) and composition 4 (100 mg/kg and 250 mg/kg doses, example #14) for protection against diet induced obesity and control (placebo) group are summarized in FIG. 6A. The mean serum leptin levels for different treatment groups supplemented with *Piper betle* (250 mg/kg, example #12) and composition 4 (100 mg/kg and 250 mg/kg doses, example #15) for treatment against diet induced obesity and control group are summarized in FIG. 6B. All the treatment groups exhibited significant reduction in serum leptin levels compared to control group of animals.

The above in vivo experimental studies suggest that extract of *Piper betle* or its compositions possess potential application for the prevention and inhibition of adipogenesis mediated diseases such as obesity.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. An oral dosage form, comprising:
   an amount of an anti-adipogenic herbal composition which is effective for inhibiting or ameliorating adipogenesis in mammals, said herbal composition comprising:
   from 33% to 67% by weight of a *Piper betle* extract, wherein the *Piper betle* extract is obtained by extraction of *Piper betle* with a solvent selected from the group consisting of:
      an alcoholic solvent containing 40% to 60% water, and
      a polar organic solvent selected from the group consisting of C3-C4 alcohols and C3-C6 ketones; and
   an effective amount of a *Dolichos biflorus* extract, wherein the *Dolichos biflorus* extract is obtained by extraction of *Dolichos biflorus* with a solvent selected from the group consisting of at least one polar organic solvent and a combination of a polar organic solvent and water,
   optionally in combination with at least one biologically acceptable excipient;
   wherein said dosage form is a tablet, soft capsule, hard capsule, pill, controlled release tablet, or polymer-coated tablet.

2. The dosage form according to claim 1,
   wherein the composition comprises *Piper betle* extract in the range of 40%-60% by weight and *Dolichos biflorus* extract in the range of 40%-60% by weight.

3. A dosage form comprising an anti-adipogenic herbal composition for inhibiting or ameliorating adipogenesis in mammals, said herbal composition consisting essentially of:
   an effective amount of a *Piper betle* extract, wherein the *Piper betle* extract is obtained by extraction of *Piper betle* with a solvent selected from the group consisting of:
      an alcoholic solvent containing 40% to 60% water, and
      a polar organic solvent selected from the group consisting of C3-C4 alcohols and C3 to C6 ketones;
   optionally, an effective amount of a *Dolichos biflorus* extract, wherein the *Dolichos biflorus* extract is obtained by extraction of *Dolichos biflorus* with a solvent selected from the group consisting of water, a polar organic solvent, and mixtures thereof;
   optionally, at least one biologically acceptable excipient;
   wherein the herbal composition further comprises one or more anti-adipogenic or anti-obesic agents selected from the group consisting of extracts of *Commiphora mulul, Boerhavia diffusa, Tribulus terrestris, Zingiber officinale*, and mixtures thereof; and
   optionally, a bio-enhancing agent or a bio-protecting agent;
   wherein said dosage form is a tablet, soft capsule, hard capsule, pill, controlled release tablet, or polymer-coated tablet.

4. The dosage form as in claim 3, wherein the composition comprises extracts of *Piper betle, Commiphora mulul, Boerhavia diffusa, Tribulus terrestris*, and *Zingiber officinale*, and further comprises said bio-enhancing agent, wherein said bio-enhancing agent comprises an extract of *Piper nigrum*.

5. The dosage form as in claim 3, wherein the composition comprises *Piper betle* extract in die range of 10-40%, *Commiphora mulul* extract in the range of 10-40%, *Boerhavia diffusa* extract in the range of 10-40%, *Tribulus terrestris* extract in the range of 10-40%, *Zingiber officinale* extract in the range of 10-40% and said extract of *Piper nigrum* in the range of 10-40%.

6. The dosage form as in claim 3, wherein said composition further comprises an effective amount of at least one additional ingredient selected from the group consisting of: a pharmaceutically, nutritionally, or dietetically acceptable antioxidant, adaptogen, anti-inflammatory agent, anti-diabetic agent, bio-protectant, trace metals and mixtures thereof.

7. The dosage form as claimed in claim 3, wherein said composition, optionally, further comprises biologically acceptable excipients, and wherein the said dosage form is a nutraceutical, pharmaceutical, or dietary form.

8. The dosage from as in claim 3, wherein the composition optionally further comprises anti-adipogenic or anti-obese agents selected from the group consisting of: an *Holoptelia integrifolia* extract, a *Garcinia cambogia* extract, a green tea extract, a green coffee bean extract, an eucalyptus plant extract, a bitter orange (*Citrus aurantium*) extract, Conjugated linoleic acid, a *Hoodia Gordonii* extract, an *Allium sativum* extract, chromium (III) complexes, DHEA, and 7-Keto-DHEA.

9. The dosage form as claimed in claim 7, wherein the dosage form is suitable for parenteral administration as suppositories.

10. The dosage form as claimed in claim 3, wherein said composition is a dietary formulation.

11. The dosage form as claimed in claim 4, wherein said composition further comprises a pharmaceutically, nutraceutically, diatetically, or veterinary acceptable additive, wherein the said additive is a binder, diluent, antioxidant, or lubricant.

12. The dosage form as claimed in claim 1, wherein the *Piper betle* extract is obtained from a plant part selected from the group consisting of leaf, seed, trunk, root and combinations thereof; and
    the *Dolichos biflorus* extract is obtained from a plant part selected from the group consisting of: leaf, seed, trunk, root and combinations thereof.

13. The dosage form as claimed in claim 1, wherein the *Piper betle* extract and the *Dolichos biflorus* extract are derived by extraction from plant parts with a solvent selected from the group consisting of water, a polar organic solvent, and a mixture thereof, wherein the solvent used for extraction of the plant parts is selected from the group consisting of methanol, ethanol, propanol, isopropanol, n-butanol, isobutanol, sec-butanol, tert-butanol, dimethyl ketone, methyl ethyl ketone, acetone, methyl isobutyl ketone, water and mixtures thereof.

14. A method for inhibiting adipogenesis and fat accumulation in a mammal, comprising administering to a said mammal an effective amount of the dosage form of claim 4, wherein said dosage form is a dietary or nutraceutical or pharmaceutical composition.

15. A method for inhibiting or treating adipogenesis in a mammal comprising administering to a said mammal an effective amount of the dosage form of claim 4.

16. The dosage form as claimed in claim 1, wherein the said composition optionally comprises anti-adipogenic or anti-obese agents selected from the group consisting of an *Holoptelia integrifolia* extract, a *Garcinia cambogia* extract, a green tea extract, a green coffee bean extract, a eucalyptus plant extract, a bitter orange (*Citrus aurantium*) extract, Conjugated linoleic acid, a *Hoodia gordonii* extract, an *Allium sativum* extract, chromium (III) complexes, DHEA, and 7-Keto-DHEA.

17. The dosage form as claimed in claim 1, wherein said composition further comprises biologically acceptable excipients, and wherein said dosage form is selected from the group consisting of:
nutraceuticals, pharmaceuticals and dietary forms.

18. The dosage form as claimed in claim 6, wherein said bio-protectant is *Curcuma longa*.

19. A method for inhibiting or preventing or treating adipogenesis in a mammal comprising administering to a said mammal an effective amount of the dosage form of claim 1.

20. A method for inhibiting adipogenesis and fat accumulation in a mammal, comprising administering to a said mammal an effective amount of the dosage form of claim 1, wherein said dosage form is a dietary or nutraceutical or pharmaceutical composition.

21. A method for inhibiting or treating adipogenesis mediated diseases in a mammal comprising administering to a said mammal an effective amount of the dosage form of claim 2.

22. A dosage form comprising an anti-adipogenic herbal composition for inhibiting adipogenesis in mammals, said dosage form comprising:
an effective amount of a *Piper betle* extract, wherein the *Piper betle* extract is obtained by extraction of *Piper betle* with a solvent selected from the group consisting of:
an alcoholic solvent containing 40% to 60% water, and
a polar organic solvent selected from the group consisting of C3-C4 alcohols and C3-C6 ketones;
an effective amount of a *Dolichos biflorus* extract, wherein the *Dolichos biflorus* extract is obtained by extraction of *Dolichos biflorus* with water or a polar organic solvent or a mixture thereof; and
an optional biologically acceptable excipient;
wherein said *Piper betle* extract and said *Dolichos biflorus* extract are the only herbal ingredients present in said anti-adipogenic herbal composition; and
wherein said dosage form is a tablet, soft capsule, hard capsule, pill, controlled release tablet, or polymer-coated tablet.

23. The dosage form as claimed in claim 22, wherein the effective amount of said *Piper betle* extract in the composition is in the range of 1% to 99% by weight.

24. The dosage form as claimed in claim 22, wherein the composition comprises *Piper betle* extract in the range of 1%-99% by weight and *Dolichos biflorus* extract in the range of from greater than 0% to 70% by weight.

25. A dosage form comprising an anti-adipogenic herbal composition for inhibiting adipogenesis in mammals, said herbal composition consisting essentially of a first herbal component and an optional biologically acceptable excipient;
said first herbal component comprising an effective amount of *Piper betle* extract obtained by extraction of *Piper betle* with at least one solvent selected from the group consisting of: polar organic solvents to obtain a solution, and an effective amount of *Dolichos biflorus* extract obtained by extraction of *Dolichos biflorus* with at least one polar organic solvent or a combination of a polar organic solvent and water;
wherein said first herbal component is prepared by a process consisting essentially of mixing said *Piper betle* extract and said *Dolichos biflorus* extract; and
wherein said dosage form is a tablet, soft capsule, hard capsule, pill, controlled release tablet, or polymer-coated tablet.

26. The dosage form as claimed in claim 1, wherein:
the *Piper betle* extract is obtained by extraction of *Piper betle* leaves; and
the *Dolichos biflorus* extract is obtained by extraction of *Dolichos biflorus* leaves.

27. An oral dosage form, comprising:
an amount of an anti-adipogenic herbal composition which is effective for inhibiting or ameliorating adipogenesis in mammals, said herbal composition comprising:
from 33% to 67% by weight of a *Piper betle* extract, wherein the *Piper betle* extract is obtained by:
extracting *Piper betle* with a solvent selected from the group consisting of at least one polar organic solvent and an aqueous alcohol containing 40% to 60% water to produce a *Piper betel* extract,
filtering the *Piper betle* extract to provide a filtered extract, and
evaporating the filtered extract to dryness at 50-60° C.; and
an effective amount of a *Dolichos biflorus* extract, wherein the *Dolichos biflorus* extract is obtained by extraction of *Dolichos biflorus* with a solvent selected from the group consisting of water, a polar organic solvent and a combination of a polar organic solvent and water, and mixtures thereof;
optionally in combination with at least one biologically acceptable excipient;
wherein said dosage form is a tablet, soft capsule, hard capsule, pill, controlled release tablet, or polymer-coated tablet.

28. The dosage form as claimed in claim 1, further comprising a second herbal component selected from the group consisting of: a *Holoptelia intergifolia* extract, a *Garcinia cambogia* extract, a green tea extract, a green coffee bean extract, a eucalyptus plant extract, a bitter orange (*Citrus aurantium*) extract, a *Hoodia gordonii* extract, an *Allium sativum* extract, and mixtures thereof.

* * * * *